United States Patent [19]

Williams

[11] Patent Number: 5,248,432
[45] Date of Patent: Sep. 28, 1993

[54] HALOGENATED ARYL ESTER DAMPING FLUIDS AND LUBRICANTS

[75] Inventor: John R. Williams, Lexington, Mass.

[73] Assignee: Charles Stark Draper Laboratory, Inc., Cambridge, Mass.

[21] Appl. No.: 862,822

[22] Filed: Apr. 3, 1992

Related U.S. Application Data

[60] Division of Ser. No. 508,277, Apr. 11, 1990, Pat. No. 5,177,252, which is a continuation-in-part of Ser. No. 358,401, May 26, 1989, abandoned, which is a continuation of Ser. No. 45,897, May 1, 1987, Pat. No. 4,835,304.

[51] Int. Cl.$^5$ ............... C10M 105/54; C10M 105/34; C10M 105/36
[52] U.S. Cl. ............................ 252/51.5 R; 252/54.6; 252/78.1
[58] Field of Search ................. 252/51.5 R, 54.6, 78.1

[56] References Cited

U.S. PATENT DOCUMENTS 3,931,325  1/1976  Doorenbos et al. ............... 260/586
3,996,200 12/1976  Doorenbos et al. ........... 260/63 HA

FOREIGN PATENT DOCUMENTS 73539  3/1983  European Pat. Off. .
089820 3/1983  European Pat. Off. .

OTHER PUBLICATIONS

Du Pont Manufacturers Brochure on Krytox Fluorinated Oils (Aug. 1986).
De Pasquale, R. I., et al, NASA, Report No. N83-10195 (Aug. 1965).
Koehler, K. E., Charles Stark Draper Laboratory, Report No. C-5413.
Lagow, R. I., Defense Technical Information Center Document, Report No. AF0SR-TR 82-1037.
Paciorek, K. J. L. et al, Ind. Eng. Chem. Prod. Res. Dev., 22, 5-8 (1983).
Persico, D. F., et al., J. Am. Chem. Soc., 107, 1197-1201 (1985).
Soloski, E. J. and Tamborski, D., J. Fluorine Chem, 11, 601-612 (1978).
Chem Abstract, 101:191,244u, Chen (1984).
Customer Search Results, CAS Search Service, The American Chemical Society, (Reg. File Search Results P116412T), 8 substances 1957-date, 26 Apr. 1989, pp. 1-19.
Chem Abstract, 91:113332c Attenuator Dispersion. Lochner, Kaspar Ger. Offen. 2,814,366 (Cl. C10M 7/04), 18 Oct. 1979.
Chem Abstract, 87:137943a Medium for Damping Mechanical and Acoustical Vibrations. Lochner, Kasper Ger. Offen. 2,549,672 (Cl. C10M3/20), 12 May 1979.
Chem Abstract, 81397r Use of Copolymers as Power Transfer and/or Damping Liquids or as Constituent of These Liquids. Secker, Frederick J. S. (Shell Internationale Research Maatschappeij N.V.) Ger. No. 1,644,951 (Cl. C 10m) 07 Jun. 1973.

*Primary Examiner*—Jerry D. Johnson
*Attorney, Agent, or Firm*—Weingarten, Schurgin, Gagnebin & Hayes

[57] ABSTRACT

The invention provides a method for lubricating inertial instruments such as gyroscopes and accelerometers which require flotation fluids for operation. An exemplary process comprises introducing a fluid which contains a halogenated aryl ring, to an inertial instrument, having an axis bearing and/or a slip ring, whereby the axis bearing and/or slip ring are lubricated and the internal sensing elements are floated by the dense fluid.

9 Claims, 1 Drawing Sheet

HALOGENATED ARYL ESTER DAMPING FLUIDS AND LUBRICANTS

This application is a divisional application of Ser. No. 07/508,277, filed Apr. 11, 1990, now U.S. Pat. No. 5,177,252 which is a continuation in part of application Ser. No. 07/358401, filed May 26, 1989, now abandoned which is a continuation of application Ser. No. 07/045897, filed May 1, 1987 now U.S. Pat. No. 4,835,304.

FIELD OF THE INVENTION

This invention relates to fluids for providing flotation and damping in floated inertial instruments, and more particularly, to a method for lubricating floated inertial instruments.

BACKGROUND OF THE INVENTION

Floated inertial instruments such as certain types of accelerometers and gyroscopes require flotation fluids for operation. Such fluids must have high densities to provide adequate flotation for structural components, and also require relatively high viscosities for good damping properties.

Presently used flotation fluids such as chlorotrifluoroethylene (CTFE), bromotrifluoroethylene (BTFE), and triazines having halogenated side chains derived from CTFE and BTFE suffer from certain disadvantages. CTFE and BTFE cannot be obtained pure, and therefore cause instrument anomalies such as gravity sensitive trends and hot storage sensitivity. Also, high molecular weight CTFE is a wax at room temperature. The triazines are of higher purity than CTFE or BTFE, but because of difficulties in purification they are not single component fluids, but contain isomers such as diastereomers and head-to-head monomer units. They are also expensive, and exhibit maximum densities in the range of only about 2.4 grams per ml.

It would be desirable to have available high density high viscosity fluids which can be readily synthesized at reasonable cost and readily purified.

SUMMARY OF THE INVENTION

The present invention overcomes many of the deficiencies of prior art flotation fluids by providing a diverse family of flotation fluids having a wide range of densities and a very wide range of viscosities, and providing these materials relatively inexpensively and in high purity. The materials of the present invention are easier to synthesize than many of the presently employed flotation fluids, and are relatively inexpensive to manufacture since they are made from inexpensive starting materials and in many instances do not require extensive purification operations. Because the starting materials can be obtained pure, the final products can also be manufactured in very high purity and thus do not suffer from the stratification which is known to occur with former flotation fluids upon standing.

Some of the materials of the invention have exceptionally high densities, in the range of 2.7 g/cc and higher, thus permitting a wide choice of structural materials for the construction of the instruments in which they are to be used. For example aluminum and aluminum composites can be used in place of beryllium with flotation fluids having sufficiently high densities and still remain floated. This is advantageous since beryllium is toxic, expensive, and not readily weldable. The higher densities of the fluids of the invention also allow higher angular momentum for the inertial instrument to be achieved for a given size unit, or the same angular momentum to be achieved for a smaller sized float. In addition, the fluids of the invention are essentially nonflammable, and hence may be used wherever a fire-resistant fluid is required. They also possess good lubricating properties.

The damping/flotation fluids of the invention are materials containing a highly halogenated aryl group connected to a highly halogenated alkyl group by an ester linkage. They are easily synthesized from readily available starting materials regardless of the orientation of the linking ester functionality. Many halogenated phenols and halogenated benzoic acids required for preparation of the claimed esters are commercially available at reasonable cost. The heavily halogenated alkyl carboxylic acids which are also needed are readily prepared in high purity and at relatively low cost by telomerization reactions and addition of alkyl halides across the double bond in halogenated ethylenes. These materials are easily purified, and the use of high levels of fluorine produces final esters having wide liquid ranges, while the use of high levels of bromine and iodine in the aryl part of the molecule produces esters of high density. Both the aryl and the alkyl portions of the final esters can be varied readily in the starting materials to achieve a wide range of densities and viscosities in the resulting esters.

The high density damping fluids of the invention have the general formula

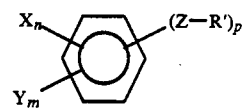

I in which X represents any of the halogens fluorine, chlorine, bromine, and iodine in any combination. The sum of the atomic masses of the halogen atoms on the phenyl ring is at least 90. The subscript n is 1–5, indicating that the aryl group contains from 1 to 5 halogen substituents. Y represents an alkyl group —R, an ether group —OR, an ester group —$CO_2R$, an aldehyde of 1–4 carbon atoms, a ketone of 1–4 carbon atoms, an acetal of 3–7 carbon atoms, a ketal of 4–7 carbon atoms, a cyano group CN, or a nitro group —$NO_2$, where R is a straight, branched, or cyclic alkyl or haloalkyl group containing 1–4 carbon atoms. Each o( these hydrocarbon-based groups may contain from 0 to t halogen substituents selected from the group consisting of F, Cl, and Br, where t for each of the hydrocarbon-based groups is the total number of hydrogen atoms contained in the corresponding unsubstituted group. The aryl group may contain up to 2 such Y substituents, as indicated by the value of the subscript m being 0–2.

By "haloalkyl" is meant an alkyl group in which at least one and preferably more than one of the hydrogen atoms have been replaced by halogens.

Z represents an ester functionality, present in either of two orientations,

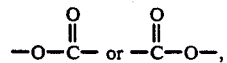

relative to the aryl and alkyl portions of the molecule, as shown in formula I.

R' is a straight, branched, or cyclic haloalkyl group containing 2-8 carbon atoms. The halogen atoms of the R' group are selected from the group consisting of F, Cl, and Br. R' contains at least one F atom, and further contains halogen atoms in place of greater than 60% of the hydrogen atoms of the corresponding unhalogenated alkyl group. The R' group contains from 0 to a maximum of 2 consecutive $CF_2$ moieties, and the sum of the atomic masses of the halogen atoms on R' is greater than 135. The compound as a whole contains at least two types of halogen atoms. Finally, the sum of the number of F and H atoms in the compound divided by the number of halogen atoms other than F in the compound is a maximum of 7. There may be from 1 to 3 Z—R' groupings on the benzene ring of formula 1, as indicated by the subscript p being 1-3.

The inventive concept also encompasses mixtures of the compounds of the invention with each other and with other materials having damping and/or lubricating properties. It further encompasses any instrument or other apparatus which includes a fluid of the invention. Examples of such apparatus are a gyroscope, an integrating pendulous accelerometer, and a pendulous integrating gyroscopic accelerometer. Such instruments include a housing, a float, and a fluid comprising a compound according to the invention, with the float being in contact with the fluid.

Further, as the compounds of the invention are lubricants as well as damping fluids, the scope of the invention includes a method for lubricating two items which are in moving contact with each other, by applying to the area of contact between them a fluid lubricant comprising a compound according to the invention. It also includes a method for damping relative motion between two elements of an apparatus, by disposing a fluid comprising a compound of the invention between the elements to damp motion of one relative to the other.

DESCRIPTION OF THE DRAWING

The invention will be better understood from a consideration of the following detailed description taken in conjunction with the drawing, in which.

Figure 1:
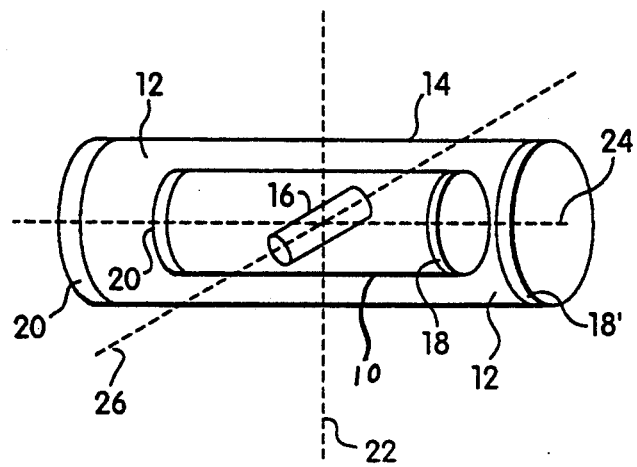
FIG. 1 is a generalized illustration of a gyroscope or integrating pendulous accelerometer, in which the fluids of the invention are used.
Figure 2:
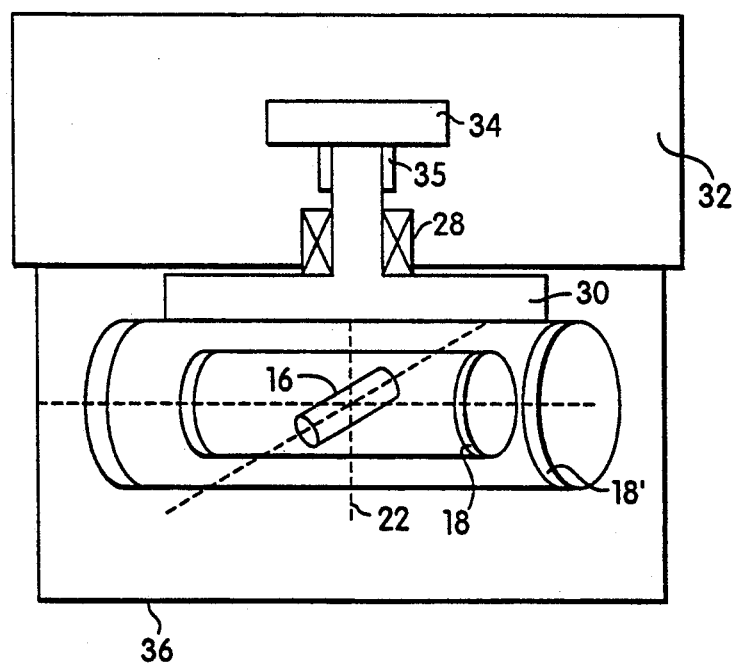
FIG. 2 is a generalized illustration of a pendulous integrating gyroscopic accelerometer, in which the fluids of the invention are used.

DETAILED DESCRIPTION OF THE INVENTION AND DESCRIPTION OF THE PREFERRED EMBODIMENTS

In formula I, X is preferably bromine, iodine, or a mixture of these two halogens, to provide high density in the resulting product ester, and the benzene ring is preferably provided with 2-5 halogen substituents.

The group Y is preferably a small alkyl group such as methyl or ethyl, and may be partially or totally halogenated An example of the latter sort of substituent is the trifluoromethyl group. Preferably the benzene ring of formula I contains no more than 1 such Y substituent.

The damping fluids of formula I are preferably aryl esters in which the group Z is

and p=1 because such materials are somewhat easier to prepare than the alkyl esters in which Z is

and p is greater than 1.

The group R' in formula I preferably contains 2-5 carbon atoms, most preferably, 3-4 carbons, and a maximum of 2 hydrogen atoms, though longer carbon chains and higher numbers of hydrogen atoms will function in the invention. Group R' is thus seen to be a highly halogenated group, preferably a perhaloalkyl group. Fluorine, chlorine, and bromine may be employed in any combination in group R', fluorine and bromine being preferred. Iodine is generally disfavored for use in group R because it tends to hydrolyze in the presence of water, metal, and/or acidic conditions, leading to a corrosive damping fluid. Group R' preferably contains at least two types of halogen atoms. High levels of fluorine are advantageous in group R' because they produce products having wide liquid ranges. The carbon atom of group R' located 8 to the ester group preferably carries at least two halogen substituents or at least one halogen and a further haloalkyl moiety, and is preferably not a —$CH_2$— group. Of course, the combinations of X on R' should be stable for the particular application in question.

A subclass of high density damping fluids encompassed within formula I are materials shown generally by formula II

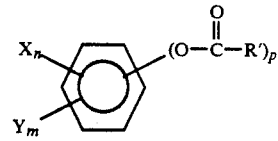

II in which X, Y, m, R', and p are the same as defined with respect to formula I above, but n is now 2-5 and Z is now defined as

so that formula II defines an aryl ester. The other preferences expressed above with respect to the compounds of formula I continue to apply to those of formula II.

A high density damping fluid encompassed by formula II is that shown in formula III

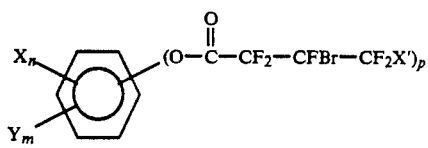

III in which X is a halogen selected from the group consisting of fluorine, chlorine, bromine, and iodine, and n=2-5. Again, the sum of the atomic masses of the halogen atoms on the phenyl ring is at least 90. In this material Y is a substituent selected from the group consisting of —R and —OR, in which R is an alkyl or haloalkyl group containing 1-2 carbon atoms. The subscript m=0-2, and p=1-2. Group X' is Br or Cl. Again, the sum of the number of F and H atoms in the compound divided by the number of halogen atoms other than F is a maximum of 7. In the material of formula III, X is preferably selected from the group consisting of bromine and iodine, n is preferably 3-4, the group Y is preferably methyl or ethyl, and m is preferably 1.

In Table I are shown structural formulae of several representative compounds of the invention which have been prepared, as well as their densities, viscosities, and freezing points, where these are known.

TABLE I

Representative Compounds Prepared and Their Properties

| # | Structure | Density (g/cc) at 135° F. | Viscosity (cp) at 135° F. | Freezing Point, °C. |
|---|---|---|---|---|
| 1. | 2,4,6-tribromophenyl — O—C(=O)—$CF_2$—CFBr—$CF_2Br$ | 2.36 | 66 | <RT |
| 2. | 2,3,4,6-tetrabromophenyl — O—C(=O)—$CF_2$—CFBr—$CF_2Br$ | 2.53 | 341 | <RT |
| 3. | 2,4,6-triiodophenyl — O—C(=O)—$CF_2$—CFBr—$CF_2Br$ | 2.70 | 978 | 50 |
| 4. | 2,6-diiodo-3-bromo-4-iodo... phenyl (I, I, Br, I substituents) — O—C(=O)—$CF_2$—CFBr—$CF_2Br$ | 2.84 | 7,555 | 57 |
| 5. | 2,6-diiodo-4-methyl... (I, I, Me, I) phenyl — O—C(=O)—$CF_2$—CFBr—$CF_2Br$ | 2.63 | 2,012 | <RT |
| 6. | 2,6-diiodo-4-ethyl... (I, I, Et, I) phenyl — O—C(=O)—$CF_2$—CFBr—$CF_2Br$ | 2.53 | 3,981 | <RT |
| 7. | 2,6-dichloro-4-ethyl... (Cl, Cl, Et, Cl) phenyl — O—C(=O)—$CF_2$—CFBr—$CF_2Br$ | 1.93 | 23 | <RT |

TABLE I-continued

Representative Compounds Prepared and Their Properties

| | Density (g/cc) at 135° F. | Viscosity (cp) at 135° F. | Freezing Point, °C. |
|---|---|---|---|
| 8. Br-C6H(Br)(Br)(Br)(O-CO-CF2-CFBr-CF2Br)(O-CO-CF2-CFBr-CF2Br) | 2.40 | 4,184 | <RT |
| 9. Br-C6H(Br)(Br)(Br)(O-CO-CF2CFBrCF2Cl) | — | — | — |

For the materials numbered 1–4 in Table I, density is a linear function of molecular weight. It is thus apparent that increasing the bromine and iodine content of these molecules increases their density proportionately. Also, it will be observed that the log of the viscosity of compounds 1–4 is linearly proportional to the molecular weight of these damping fluids. Thus, knowing the molecular weights, densities, and viscosities of several of the damping fluids in a series permits accurate estimation of the density and viscosity to be achieved in similar materials having different halogen substitutions. This predictability of properties is confirmed by the observation that the logs of the viscosities of compounds 3, 5, and 6 of Table I are linearly related to the number of carbons attached to the aryl ring, and by the further observation that the viscosity of 4.5 cp predicted for $Cl_3C_6H_2$—O—CO—$CF_2$—CFBr—$CF_2Br$ based on the data for compounds 1–4 of Table I, and the viscosity measured for compound 7 of Table I, when plotted on the log scale of semi-log paper versus the number of carbons attached to the aryl ring give a line which is parallel to that obtained by the similar plot of viscosity data for compounds 3, 5, and 6.

The damping fluids of the invention are readily synthesized by well known chemical reactions as shown in the equations below.

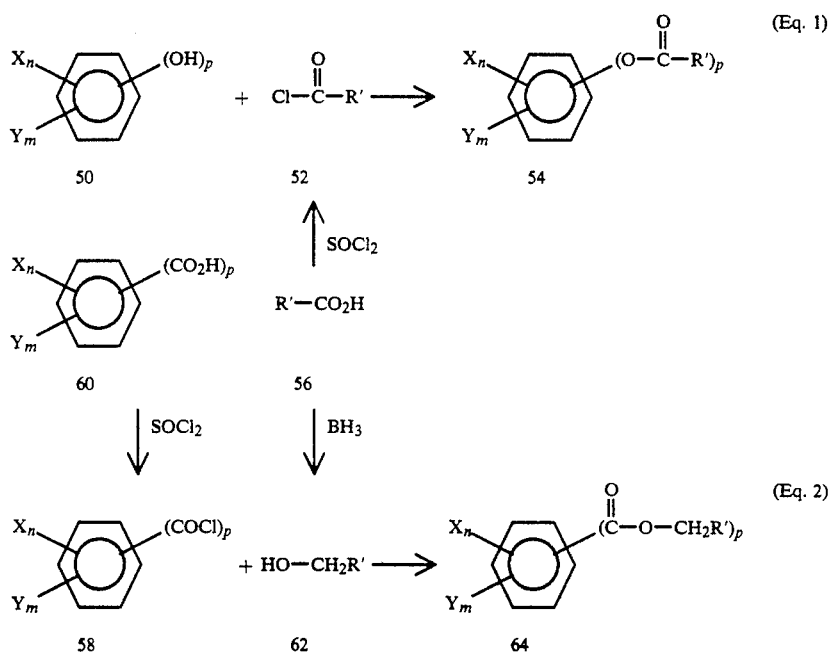

Equation 1 shows the reaction of a substituted phenol 50 with an acid chloride 52 to yield a substituted aryl ester 54. The acid chloride is produced by the reaction of the corresponding carboxylic acid 56 with thionyl chloride. Equation 2 shows the reaction of a substituted acid chloride 58 (derived from the corresponding substituted benzoic acid 60) with an alcohol 62 to yield an alkyl ester 64. Alcohol 62 is derived from the reduction of carboxylic acid 56 with borane, or by other suitable reduction reactions as known to those skilled in the art.

Numerous substituted phenols 50 are known in the chemical literature. A representative listing of some of these, compiled from Beilstein, is shown in Table II, which also includes the appropriate Beilstein references. Similarly, many substituted benzoic acids 60 are known in the chemical literature, and a representative listing of some of these is presented in Table III, which is also compiled from Beilstein. The materials shown in Tables II and III, as well as the many other similar materials of the respective classes known to the art, are appropriate for use as the precursors of the aryl portion of the product esters in the synthesis of the fluids of the invention.

TABLE II

Representative Halogen-Substituted Phenols

| Substituted Phenol | | Beilstein Reference | |
|---|---|---|---|
| -dichloro-difluoro | 5 | IV | 663 |
| -2-bromo-6-chloro-4-iodo | 6 | I | 111 d |
| -4-bromo-2-chloro-6-iodo | 6 | II | 201 f |
| -2-bromo-4-chloro-3-iodo-6-nitro | 6 | III | 853 a |
| -2-bromo-4,6-dichloro | 6 | | 201 j |
| | 6 | II | 187 i |
| | 6 | III | 751 d |
| -3-bromo-2,6-dichloro | 6 | III | 751 h |
| -4-bromo-2,5-dichloro | 6 | III | 752 a |
| -4-bromo-2,6-dichloro | 6 | | 202 a |
| | 6 | I | 106 b |
| | | II | 187 k |
| | | III | 752 b |
| -2-bromo-4,6-difluoro | 6 | IV | 1058 |
| -2-bromo-4,6-diiodo | 6 | III | 788 e |
| -4-bromo-2,6-diiodo | 6 | II | 202 n |
| | | III | 788 h |
| -3-bromo-2,4,5,6-tetrachloro | 6 | I | 106 e |
| | | II | 188 e |
| -2-bromo-3,4,6-trichloro | 6 | III | 752 d |
| -3-bromo-2,4,5-trichloro | 6 | III | 752 f |
| -3-bromo-2,4,6-trichloro | 6 | | 202 b |
| | | I | 106 c |
| | | II | 188 b |
| | | III | 752 j |
| -4-bromo-2,3,6-trichloro | 6 | III | 752 i |
| -6-bromo-2,3,4-trichloro | 6 | III | 752 e |
| -3-bromo-2,4,6-trichloro-5-nitro | 6 | II | 234 e |
| -2-chloro-4,6-diiodo | 6 | I | 111 o |
| | | II | 202 b |
| | | III | 787 d |
| -4-chloro-2,6-diiodo | 6 | I | 112 d |
| | | II | 202 j |
| | | III | 787 i |
| -2-fluoro-4,6-diiodo | 6 | IV | 1084 |
| -4-fluoro-2,6-diiodo | 6 | III | 786 l |
| -3-fluoro-2,4-diiodo-6-nitro | 6 | III | 853 g |
| -2,4-dibromo-3-chloro | 6 | II | 189 i |
| -2,4-dibromo-6-chloro | 6 | | 203 e |
| | | II | 189 k |
| | | III | 758 b |
| -2,6-dibromo-4-chloro | 6 | I | 107 c |
| | | II | 190 a |
| | | III | 758 f |
| -3,4-dibromo-5-chloro | 6 | II | 190 e |
| -3,5-dibromo-2-chloro | 6 | II | 190 g |
| -3,5-dibromo-4-chloro | 6 | II | 190 i |
| -3,4-dibromo-5-chloro-2,6-diiodo | 6 | II | 203 c |
| -3,5-dibromo-2-chloro-4,6-diiodo | 6 | II | 203 a |
| -3,5-dibromo-4-chloro-2,6-diiodo | 6 | II | 203 d |
| -3,4-dibromo-3-chloro-6-iodo | 6 | III | 785 i |
| -2,6-dibromo-3-chloro-4-iodo | 6 | III | 786 a |
| -4,6-dibromo-3-chloro-2-iodo | 6 | III | 785 h |
| -3,5-dibromo-4-chloro-2-iodo-6-methyl | 6 | II | 337 g |
| -2,3-dibromo-4,6-dichloro | 6 | II | 191 f |
| -2,4-dibromo-3,6-dichloro | 6 | III | 758 i |
| -2,6-dibromo-3,4-dichloro | 6 | III | 759 d |
| -3,4-dibromo-2,6-dichloro | 6 | II | 190 k |
| | | III | 759 e |
| -3,5-dibromo-2,4-dichloro | 6 | II | 191 b |
| -3,5-dibromo-2,6-dichloro | 6 | II | 191 d |
| -3,6-dibromo-2,4-dichloro | 6 | II | 191 f |
| -4,6-dibromo-2,3-dichloro | 6 | III | 759 b |
| -3,5-dibromo-2,4-dichloro-6-iodo | 6 | II | 201 d |
| -3,5-dibromo-2,6-dichloro-4-iodo | 6 | II | 201 n |
| -3,5-dibromo-2,4-diiodo-6-methyl | 6 | II | 338 b |
| -2,4-dibromo-5-fluoro | 6 | III | 757 b |
| -2,4-dibromo-6-fluoro | 6 | III | 757 c |
| -2,6-dibromo-4-fluoro | 6 | III | 757 d |
| -2,4-dibromo-3-fluoro-6-nitro | 6 | III | 849 f |
| -2,6-dibromo-3-fluoro-4-nitro | 6 | III | 849 g |
| -4,6-dibromo-3-fluoro-2-nitro | 6 | III | 849 e |
| -2,4-dibromo-6-iodo | 6 | II | 201 i |
| -2,6-dibromo-4-iodo | 6 | I | 111 f |
| | | III | 785 e |
| -2,4-dibromo-3-iodo-6-nitro | 6 | III | 853 b |
| -2,6-dibromo-3-iodo-4-nitro | 6 | III | 853 c |
| -2,5-dibromo-3,4,6-trichloro | 6 | III | 759 f |
| -2,6-dibromo-3,4,5-trichloro | 6 | II | 191 h |
| -3,4-dibromo-2,5,6-trichloro | 6 | II | 191 i |
| | | III | 759 g |
| -3,5-dibromo-2,4,6-trichloro | 6 | II | 191 j |
| -3,5-dibromo-2,4,6-triiodo | 6 | II | 205 d |
| -3,6-dichloro-2,4-diiodo | 6 | IV | 1085 |
| -2,4-dichloro-3-fluoro | 6 | IV | 958 |
| -2,4-dichloro-5-fluoro | 6 | IV | 959 |
| -2,4-dichloro-6-fluoro | 6 | IV | 959 |
| -2,5-dichloro-4-fluoro | 6 | IV | 959 |
| -2,6-dichloro-4-fluoro | 6 | III | 715 k |
| | | IV | 959 |
| -3,5-dichloro-4-fluoro | 6 | IV | 960 |
| -4,5-dichloro-2-fluoro | 6 | IV | 960 |
| -2,4-dichloro-5-iodo | 6 | III | 782 b |
| -2,4-dichloro-6-iodo | 6 | II | 200 l |
| | | III | 781 k |
| -2,6-dichloro-4-iodo | 6 | I | 110 c |
| -pentabromo | 6 | | 206 e |
| | | I | 10 j |
| | | II | 197 d |
| | | III | 766 i |
| | | IV | 1069 |
| -pentachloro | 6 | | 144 b |
| | | I | 104 f |
| | | II | 182 h |
| | | III | 731 b |
| | | IV | 1025 |
| -pentafluoro | 6 | IV | 782 |
| -2,3,4,5-tetrabromo-6-chloro | 6 | II | 196 j |
| -2,3,4,6-tetrabromo-5-chloro | 6 | II | 197 a |
| | | III | 766 h |
| -2,3,5,6-tetrabromo-4-chloro | 6 | II | 197 b |
| -2,3,4,6-tetrabromo-5-methoxy | 6 | II | 821 f |
| -2,3,4,6-tetrabromo-5-fluoro | 7 | III | 535 c |
| -2,3,4,6-tetrabromo-5-iodo | 6 | II | 202 b |
| -2,3,4,6-tetrabromo-5-nitro | 6 | | 248 k |
| | | II | 236 j |
| -2,3,4,5-tetrabromo-6-methyl | 6 | | 362 f |
| | | I | 177 f |
| | | II | 337 n |
| | | III | 1272 e |
| -2,3,4,5-tetrachloro | 6 | II | 182 b |
| | | III | 729 e |
| | | IV | 1020 |
| -2,3,4,6-tetrachloro | 6 | II | 193 d |
| | | II | 182 d |
| | | III | 729 f |
| | | IV | 1021 |
| -2,3,5,6-tetrachloro | 6 | II | 182 f |
| | | III | 730 i |
| | | IV | 1025 |
| -2,3,4,6-tetrachloro-5-iodo | 6 | I | 110 l |
| | | III | 783 k |
| -2,3,5,6-tetrachloro-4-iodo | 6 | I | 110 n |
| -2,3,4,5-tetrachloro-6-methoxy | 6 | III | 4253 c |
| | | IV | 5620 |
| -2,3,4,5-tetrachloro-6-methyl | 6 | I | 175 e |
| -2,3,4,6-tetrachloro-5-nitro | 6 | II | 232 b |
| -2,3,4,5-tetraiodo | 6 | IV | 1088 |
| -2,3,4,6-tetraiodo | 6 | IV | 1089 |
| -2,3,4-tribromo | 6 | II | 192 a |
| -2,3,5-tribromo | 6 | | 203 g |
| | | II | 192 c |
| | | III | 759 k |
| -2,4,5-tribromo | 6 | II | 192 e |
| | | | 760 c |
| -2,4,6-tribromo | 6 | | 203 i |
| | | I | 107 e |

TABLE II-continued

Representative Halogen-Substituted Phenols

| | | | |
|---|---|---|---|
| | | II | 192 g |
| | | III | 760 f |
| | | IV | 1067 |
| -3,4,5-tribromo | 6 | II | 195 a |
| -2,3,4-tribromo-6-chloro | 6 | II | 195 i |
| -2,3,6-tribromo-4-chloro | 6 | II | 195 c |
| -2,4,6-tribromo-3-chloro | 6 | II | 195 g |
| -3,4,6-tribromo-2-chloro | 6 | II | 195 c |
| -2,4,6-tribromo-3-chloro-5-iodo | 6 | II | 202 a |
| -2,4,6-tribromo-3-chloro-5-methoxy | 6 | II | 821 d |
| -2,3,5-tribromo-4-chloro-6-methyl | 6 | II | 336 g |
| | | III | 1272 b |
| -2,3,6-tribromo-4-chloro-5-nitro | 6 | II | 236 h |
| -2,3,5-tribromo-4,6-dichloro | 6 | II | 195 j |
| -2,4,5-tribromo-3,6-dichloro | 6 | III | 765 h |
| -2,4,6-tribromo-3,5-dichloro | 6 | | 206 a |
| | | II | 196 a |
| -3,4,5-tribromo-2,6-dichloro | 6 | II | 196 c |
| -2,3,5-tribromo-4,6-diiodo | 6 | II | 203 f |
| -2,4,6-tribromo-3,5-diiodo | 6 | II | 203 j |
| -3,4,5-tribromo-2,6-diiodo | 6 | II | 203 h |
| -2,4,6-tribromo-3-fluoro | 6 | III | 765 a |
| -2,4,6-tribromo-3-iodo | 6 | III | 786 c |
| -3,4,6-tribromo-2-iodo | 6 | III | 786 b |
| -2,4,6-tribromo-3-iodo-5-methoxy | 6 | II | 821 k |
| -2,4,6-tribromo-3-iodo-5-nitro | 6 | II | 238 k |
| -3,4,5-tribromo-2-iodo-6-methyl | 6 | II | 337 i |
| -2,3,4-tribromo-6-methoxy | 6 | | 786 a |
| | | I | 390 j |
| | | III | 4260 c |
| -2,3,5-tribromo-4-methyl | 6 | II | 386 a |
| -2,3,4-tribromo-4-nitro | 6 | III | 851 a |
| -2,3,4-trichloro | 6 | II | 179 h |
| | | III | 716 b |
| -2,3,5-trichloro | 6 | II | 180 a |
| | | III | 716 f |
| -2,3,6-trichloro | 6 | | 190 f |
| | | II | 180 c |
| | | III | 716 h |
| | | IV | 962 |
| -2,4,5-trichloro | 6 | II | 180 c |
| | | III | 717 d |
| | | IV | 962 |
| -2,4,6-trichloro | 6 | | 190 i |
| | | I | 103 l |
| | | II | 181 a |
| | | III | 722 b |
| | | IV | 1005 |
| -3,4,5-trichloro | 6 | II | 181 e |
| | | III | 729 a |
| -2,4,6-trichloro-3-fluoro | 6 | III | 729 c |
| -2,3,5-trichloro-4-iodo | 6 | | 209 h |
| -2,3,6-trichloro-4-iodo | 6 | | 209 h |
| | | I | 110 i |
| -2,4,6-trichloro-3-iodo | 6 | I | 110 g |
| | | III | 783 i |
| -2,3,4-trichloro-5-methoxy | 6 | IV | 568 c |
| -2,3,4-trichloro-6-methyl | 6 | I | 204 d |
| -2,3,5-trichloro-4-nitro | 6 | | 242 c |
| -2,3,5-triiodo | 6 | | 211 k |
| | | IV | 1085 |
| -2,4,6-triiodo | 6 | | 211 n |
| | | I | 112 f |
| | | II | 203 k |
| | | III | 788 i |
| | | IV | 1085 |
| -3,4,5-triiodo | 6 | IV | 1088 |
| -2,4,6-triiodo-3-methoxy | 6 | III | 4343 c |
| | | IV | 5689 |
| -2,4,6-triiodo-3-methyl | 6 | | 385 a |
| | | I | 191 j |
| | | III | 1325 b |
| | | IV | 2075 |
| -2,4,6-triiodo-3-nitro | 6 | II | 239 d |
| | | III | 853 i |
| Substituted Benzene | | | |
| -1,2-dihydroxy-4-iodo | | | 821 |
| -1,3-dihydroxy-5-iodo | 6 | II | 821 |
| -1,4-dihydroxy-2-iodo | 56 | | 667 |
| -2,4-dihydroxy-1-iodo | 6 | II | 821 |
| -1,2-dihydroxy-3,4,5,6-tetrabromo | 6 | II | 788 |
| -1,2-dihydroxy-3,4,5,6-tetrachloro | 6 | II | 787 |
| -1,3-dihydroxy-2,4,5,6-tetrachloro | 6 | II | 819 |
| -1,4-dihydroxy-2,3,5,6-tetrachloro | 6 | II | 846 |
| -1,4-dihydroxy-2,3,4,6-tetraiodo | 6 | I | 417 |
| -1,3-dihydroxy-2,4,6-tribromo | 6 | | 822 |
| -1,4-dihydroxy-2,3,5-tribromo | 6 | II | 848 |
| -1,2-dihydroxy-3,4,5-trichloro | 6 | I | 389 |
| -2,4-dihydroxy-1,3,5-trichloro | 6 | | 82 |
| -1,2,3-trichloro-4,5,6-trihydroxy | 6 | | 1084 |
| -1,2,4-trichloro-3,5,6-trihydroxy | 6 | II | 1072 |
| -1,3,5-trichloro-2,4,6-trihydroxy | 6 | II | 1144 |

| | Reference |
|---|---|
| -1,4-dihydroxy-2-iodo | J.A.C.S. 56, 667 |

TABLE III

Representative Halogen-Substitiuted Benzoic Acids

| Substituted Benzoic Acid | | Beilstein Reference | |
|---|---|---|---|
| -2-bromo-3-chloro | 9 | | 355 f |
| -2-bromo-4-chloro | 9 | | 355 i |
| -2-bromo-5-chloro | 9 | | 355 l |
| | | III | 1426 o |
| | | IV | 1027 |
| -2-bromo-6-chloro | 9 | | 356 a |
| -3-bromo-2-chloro | 9 | | 356 f |
| | | III | 1426 g |
| -3-bromo-4-chloro | 9 | | 356 i |
| | | II | 236 j |
| | | III | 1427 a |
| -2-bromo-3-chloro-5-iodo | 9 | IV | 1043 |
| -2-bromo-5-chloro-3-iodo | 9 | IV | 1043 |
| -3-bromo-2-chloro-5-iodo | 9 | IV | 1043 |
| -3-bromo-5-chloro-2-iodo | 9 | IV | 1043 |
| -5-bromo-2-chloro-3-iodo | 9 | IV | 1043 |
| -5-bromo-3-chloro-2-iodo | 9 | IV | 1043 |
| -4-bromo-2-chloro-3-methoxy | 10 | III | 260 a |
| -5-bromo-2-chloro-4-methyl | 9 | | 499 j |
| -2-bromo-3,5-dichloro | 9 | III | 1427 d |
| -3-bromo-2,5-dichloro | 9 | IV | 1027 |
| -3-bromo-4,5-dichloro | 9 | III | 1427 c |
| -4-bromo-2,5-dichloro | 9 | | 357 g |
| -4-bromo-3,5-dichloro | 9 | III | 1428 a |
| -5-bromo-2,3-dichloro | 9 | IV | 1027 |
| -5-bromo-2,4-dichloro | 9 | III | 1427 f |
| -4-bromo-3,5-dichloro-2-nitro | 9 | III | 1771 d |
| -2-bromo-3,5-diiodo | 9 | IV | 1044 |
| -3-bromo-2,5-diiodo | 9 | IV | 1044 |
| -5-bromo-2,3-diiodo | 9 | IV | 1044 |
| -3-bromo-5-fluoro | 9 | III | 1426 c |
| -3-bromo-4-fluoro | 9 | III | 1562 d |
| -2-bromo-3,4,5,6-tetrachloro | 9 | IV | 1027 |
| -4-bromo-2,3,5,6-tetrachloro | 9 | | 357 i |
| -4-bromo-2,3,5 (or 2,3,6)-trichloro | 9 | | 357 h |
| -2-chloro-3,5-diiodo | 9 | III | 1455 f |
| -3-chloro-2,5-diiodo | 9 | IV | 1044 |
| -4-chloro-3,5-diiodo | 9 | III | 1455 g |
| -5-chloro-2,3-diiodo | 9 | IV | 1044 |
| -2-chloro-4-fluoro | 9 | III | 1374 d |
| -3-chloro-2,4,6-triiodo | 9 | | 368 a |
| -2-chloro-3,4,5,6-tetrafluor | 9 | IV | 998 |
| -2,3-dibromo | 9 | | 357 j |
| | | I | 146 k |
| | | IV | 1027 |
| -2,4-dibromo | 9 | | 358 b |
| | | I | 146 l |
| | | II | 237 a |
| | | IV | 1027 |
| -2,5-dibromo | 9 | | 358 h |
| | | I | 147 a |
| | | II | 237 d |
| | | III | 1428 b |
| | | IV | 1027 |
| -2,6-dibromo | 9 | | 358 l |
| | | I | 147 b |
| | | II | 237 e |
| | | III | 1428 f |
| | | IV | 1028 |
| -3,4-dibromo | 9 | | 359 f |

TABLE III-continued
Representative Halogen-Substituted Benzoic Acids

| Substituted Benzoic Acid | | Beilstein Reference | |
|---|---|---|---|
| | | I | 147 c |
| | | II | 237 o |
| | | III | 1428 g |
| | | IV | 1028 |
| -3,5-dibromo | 9 | | 359 k |
| | | I | 147 f |
| | | II | 237 p |
| | | III | 1429 c |
| | | IV | 1028 |
| -2,3-dibromo-5-chloro | 9 | IV | 1029 |
| -2,4-dibromo-6-chloro | 9 | | 360 f |
| | | III | 1429 f |
| -2,5-dibromo-3-chloro | 9 | IV | 1029 |
| -3,5-dibromo-2-chloro | 9 | III | 1429 g |
| -3,5-dibromo-4-chloro | 9 | II | 238 b |
| -3,5-dibromo-4-fluoro | 9 | IV | 1029 |
| -2,3-dibromo-5-iodo | 9 | IV | 1044 |
| -2,5-dibromo-3-iodo | 9 | IV | 1043 |
| -3,5-dibromo-2-iodo | 9 | III | 1453 c |
| | | IV | 1043 |
| -2,3-dichloro-5-iodo | 9 | IV | 1042 |
| -2,5-dichloro-3-iodo | 9 | IV | 1042 |
| -3,5-dichloro-2-iodo | 9 | IV | 1042 |
| -3,6-dichloro-2-iodo | 9 | III | 1452 f |
| -2,3-diiodo | 9 | IV | 1044 |
| -2,4-diiodo | 9 | | 367 k |
| | | IV | 1044 |
| -2,5-diiodo | 9 | I | 149 i |
| | | IV | 1044 |
| -3,4-diiodo | 9 | | 3671 |
| | | I | 149 k |
| | | II | 241 m |
| -3,5-diiodo | 9 | | 367 m |
| | | I | 149 l |
| | | III | 1454 g |
| -3-fluoro-2-iodo | 9 | III | 1451 f |
| -4-fluoro-3-iodo | 9 | IV | 1041 |
| -2,3,4,5-tetrabromo | 9 | II | 239 a |
| -2,3,4,6-tetrabromo | 9 | | 362 f |
| | | I | 148 b |
| -2,3,4,5-tetrachloro | 9 | | 346 h |
| | | III | 1381 c |
| | | IV | 1010 |
| -2,3,4,6-tetrachloro | 9 | IV | 1011 |
| -2,3,4,5-tetrachloro-6-iodo | 9 | IV | 1043 |
| -2,3,4-tribromo | 9 | I | 147 g |
| -2,3,5-tribromo | 9 | | 360 g |
| | | I | 147 h |
| -2,4,5-tribromo | 9 | | 360 h |
| | | I | 147 j |
| | | III | 1430 a |
| -2,4,6-tribromo | 9 | | 360 i |
| | | I | 147 k |
| | | II | 238 c |
| | | III | 1430 b |
| | | IV | 1029 |
| -3,4,5-tribromo | 9 | | 361 f |
| | | I | 148 a |
| | | III | 1431 a |
| -2,3,4-trichloro | 9 | | 345 b |
| | | IV | 1009 |
| -2,3,5-trichloro | 9 | | 345 c |
| | | II | 229 n |
| | | III | 1380 b |
| | | IV | 1009 |
| -2,3,6-trichloro | 9 | | 345 h |
| | | III | 1380 c |
| | | IV | 1009 |
| -2,4,5-trichloro | 9 | | 345 i |
| | | I | 141 k |
| | | III | 1380 d |
| | | IV | 1010 |
| -2,4,6-trichloro | 9 | | 345 m |
| | | III | 1381 a |
| | | IV | 1010 |
| -3,4,5-trichloro | 9 | | 346 d |
| | | II | 230 a |
| | | IV | 1010 |
| -2,3,5-triiodo | 9 | I | 150 a |
| | | III | 1456 a |
| | | IV | 1044 |
| -2,4,5-triiodo | 9 | I | 150 b |
| -2,4,6-triiodo | 9 | III | 1456 f |
| -2-4,6-triiodo | | IV | 1045 |
| -3,4,5-triiodo | 9 | | 367 n |
| | | III | 1457 b |
| -2,3,4-triiodo-6-nitro | 9 | II | 278 k |

The fluids of the invention may be mono, di, or triesters as indicated in formula I, and in the case of di- and triesters, they may contain the ester linkage Z in both orientations simultaneously within the same compound. Equation 3 shows the reaction of a substituted hydroxybenzoic acid 66 with alcohol 62 to yield intermediate phenolic ester 68, and subsequent reaction of this material with acid chloride 52 to yield the final product 70, which possesses both aryl and alkyl ester moieties.

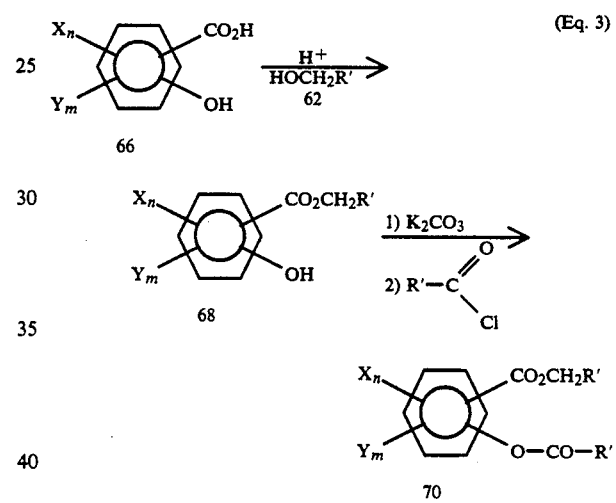

(Eq. 3)

In equation 3 it is not necessary that R' be the same in each step of the overall sequence.

Many hydroxybenzoic acids are known in the chemical literature, and a representative listing of some of these materials, compiled from Beilstein, is presented in Table IV below. Such materials are useful as precursors of the aryl portion of the halogenated mixed esters 70 in the synthesis of these materials.

TABLE IV
Representative Halogenated Hydroxybenzoic Acids

| Substituted Benzoic Acid | | Beilstein Reference | |
|---|---|---|---|
| -3-bromo-5-chloro-2,4-dihydroxy | 10 | III | 1379 d |
| -5-bromo-3-chloro-2,4-dihydroxy | 10 | III | 1379 f |
| -3 or -4-bromo-2-chloro-5-hydroxy | 10 | | 145 b |
| -4-bromo-2-chloro-3-hydroxy | 10 | III | 259 e |
| -6-bromo-2-chloro-3-hydroxy | 10 | | 145 d |
| -4-bromo-2,3,5-trichloro-6-hydroxy | 10 | III | 180 e |
| -3-bromo-5-chloro-2,4-dihydroxy | 10 | III | 1379 d |
| -5-bromo-3-chloro-2,4-dihydroxy | 10 | III | 1379 f |
| -3 or -4-bromo-2-chloro-5-hydroxy | 10 | | 145 b |
| -4-bromo-2-chloro-3-hydroxy | 10 | III | 259 p |
| -6-bromo-2-chloro-3-hydroxy | 10 | | 145 d |
| -5-chloro-2-hydroxy-5-iodo | 10 | | 113 c |
| | | II | 65 i |
| -2,4 or -2,6-dibromo-3,5-dihydroxy | 10 | III | 1450 y |
| -3,5-dibromo-2,4-dihydroxy | 10 | | 382 f |
| | | I | 179 e |
| | | II | 255 e |

TABLE IV-continued

Representative Halogenated Hydroxybenzoic Acids

| Substituted Benzoic Acid | Beilstein Reference | | |
|---|---|---|---|
| -3,5-dibromo-2,6-dihydroxy | 10 | I | 186 e |
| -4,5-dibromo-2,3-dihydroxy | 10 | I | 175 e |
| -2,4-dibromo-5-hydroxy | 10 | | 145 f |
| -2,4-dibromo-6-hydroxy | 10 | | 112 u |
| | | I | 49 h |
| -3,5-dibromo-2-hydroxy | 10 | | 109 i |
| | | I | 49 d |
| | | II | 64 c |
| | | III | 181 q |
| | | IV | 222 |
| 3,5-dibromo-4-hydroxy | 10 | | 179 b |
| | | I | 79 b |
| | | II | 104 c |
| | | III | 366 e |
| | | IV | 475 |
| -2,6-dibromo-3,4,5-trihydroxy | 10 | | 490 d |
| | | I | 251 e |
| | | II | 347 g |
| -2,4-dihydroxy-3,5-diiodo | 10 | II | 255 y |
| | | III | 179 t |
| -2,3,4,5-tetrabromo-6-hydroxy | 10 | III | 186 g |
| -2,3,5,6-tetrabromo-4-hydroxy | 10 | IV | 47 b |
| -2,3,4,6-tetrachloro-5-hydroxy | 10 | | 144 e |
| -2,3,6-tribromo-4,5-dihydroxy | 10 | | 401 d |
| | | I | 193 b |
| -2,4,6-tribromo-3,5-dihydroxy | 10 | | 406 j |
| -2,4,6-tribromo-3-hydroxy | 10 | | 145 h |
| | | II | 84 d |

The halogenated carboxylic acids 56 which serve as the precursors for the halogenated acid chlorides 52 and halogenated alcohols 62, which in turn provide the alkyl portion of the ester of the invention as shown in equations 1 and 2, are prepared in any of the several ways known to the art. For example, perfluoro carboxylic acids containing up to 8 carbon atoms are commercially available from 3M by electrochemical fluorination of the corresponding alkyl carboxylic acids. They can also be prepared by a telomerization reaction involving trifluoroiodomethane and tetrafluoroethylene as shown in Equation 4.

$$CF_3I + nCF_2=CF_2 \xrightarrow{} CF_3(CF_2-CF_2)_nI \xrightarrow{\text{fuming } H_2SO_4}$$

$$CF_3(CF_2CF_2)_{n-1}CF_2CO_2H$$

(Eq. 4)

Halogenated alkyl carboxylic acids 56 containing mixed halogens are prepared in various ways, the most widely applicable being telomerization of substituted halogenated ethylenes 72 with halogen containing materials 74 and/or addition of 74 across the double bond of 72. to yield a mixture 76 of adduct and telomers, y being 1 for the adduct and greater than 1 for telomers, followed by separation and hydrolysis to yield the final halogenated carboxylic acids 78 as shown in equation 5 below.

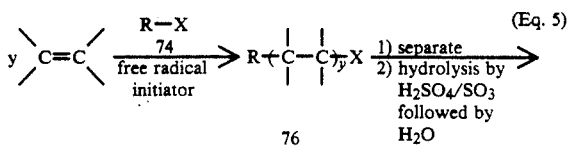

(Eq. 5)

76

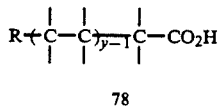

78

The halogen-containing material 74 employed in the reaction shown in equation 5 is generally an alkyl halide, but may also be a mixed halogen such as ICl, or IBr, or a material capable of providing chlorine atoms, such as sulfuryl chloride, $SO_2Cl_2$. Table v below provides a list of representative halogenated ethylenes useful in the reaction shown in equation 5 for the preparation of halogenated alkyl carboxylic acids 56.

TABLE V

Representative Halogenated Ethylenes
Useful for Preparation of R'—CO$_2$H

| | |
|---|---|
| CFCl=CFCl | CHCl=CHCl |
| CF$_2$=CFCl | CF$_2$=CH$_2$ |
| CF$_2$=CCl$_2$ | CF$_2$=CHCl |
| CF$_2$=CF$_2$ | CF$_2$=CHF |
| CCl$_2$=CCl$_2$ | CHCl=CCl$_2$ |
| CFBr=CF$_2$ | CHBr=CF$_2$ |
| CFBr=CFBr | CH$_2$=CClF |
| CF$_2$=CFBr | |
| CF$_3$—CCl=CCl$_2$ | CF$_3$—CBr=CH$_2$ |
| CF$_3$—CCl=CF$_2$ | CF$_3$CH=CF$_2$ |
| CF$_3$—CF=CF$_2$ | CF$_3$CH=CF$_2$ |
| (CF$_3$)$_2$C=CF$_2$ | CF$_2$Br—CH=CF$_2$ |
| CF$_2$Br—CBr=CF$_2$ | CF$_2$Br—CF=CF$_2$ |
| CF$_3$—CBr=CFBr | CCl$_3$—CF=CHCl |
| CF$_2$Cl—CF=CF$_2$ | |
| CF$_3$—CF=CF—CF$_3$ | |
| CF$_3$—CCl=CCl—CF$_3$ | |
| C$_2$F$_5$—CF=CF$_2$ | |
| CF$_3$CH=CFCH$_3$ | |

Table VI below provides a listing of representative halogenated alkyls 74 useful for the preparation of halogenated alkyl carboxylic acids 56 via the reaction shown in equation 5.

TABLE VI

Representative Halogenated Alkyls
Useful for Preparation of R'—CO$_2$H

| | |
|---|---|
| CCl$_3$—Br | (CF$_3$)$_2$CF—I |
| CCl$_3$—I | CF$_2$Br—CFClBr |
| CF$_3$—I | CF$_2$Cl—CFCl—I |
| CF$_2$Br$_2$ | CF$_3$CClBr$_2$ |
| CF$_2$ClBr | CF$_3$CBr$_3$ |
| C$_2$F$_5$I | CF$_3$CCl$_3$ |
| CF$_2$I—CF$_2$I | CF$_2$Br—CF$_2$I |
| C$_3$F$_7$I | |

In general, any of the olefins shown in Table V (and also many others known to those skilled in the art and shown in the literature) may be employed in the reaction of equation 5, to react with any of the materials listed in Table VI (as well as many other halogenated alkyls known to the art and shown in the chemical literature), so long as the ratio of hydrogen atoms to carbon atoms in the resulting product does not exceed 1. The compounds 76 are produced as a mixture of materials, the complexity of which is determined by the particular chemicals being reacted, and by the severity of the reaction conditions. In the adduct/telomer mixture 76, y is generally between 1 and 10 and the direction of olefin addition is generally orderly, though in some cases halogens on the olefinic component 72 may be shifted. The mixture 76 is purified by chromatography or careful distillation, to yield the separate adducts and telomers in a reasonably pure form. A desired pure adduct or telomer is then selected and hydrolyzed to yield the halogenated carboxylic acid 78. The hydrolysis reaction may cause oxidation of both ends of the material undergoing reaction, depending on its chemical constitution. In practice, a mixture of carboxylic acids is generally produced in the hydrolysis reaction, and these are converted to their methyl esters, which are in turn purified by chromatography or distillation and then hydrolyzed back to the desired carboxylic acid. The hydrolysis step generally employs either fuming sulfuric acid or concentrated (98%) sulfuric acid, and employs selected times and temperatures, depending on the particular material being hydrolyzed.

Some examples of the preparation of halogenated alkyl carboxylic acids 56 by the reaction shown in equation 5 are given below.

In Example 1, trifluorobromoethylene 80 is shown reacting with sulfuryl chloride in the presence of a free radical initiator such as azobisisobutyronitrile to yield a mixture of adducts and telomeric species represented by formulae 82 and 84. The bromine at the chain end in material 84 is derived from the starting material 80. This mixture is carefully fractionally distilled, several times if necessary, to yield ultimately several fractions of separated materials, each having high purity. One or more of these is selected for further work. In the example, a chlorine-terminated telomer 86 containing 2 monomer units is shown as having been selected for further reaction. Material 86 is first hydrolyzed with fuming sulfuric acid, then treated with methanol and finally the reaction mixture is purified by distillation to yield the methyl ester 88, which is either hydrolyzed to the corresponding carboxylic acid 90 or converted directly by means of thionyl chloride and pyridine to the final acid chloride product 92.

EXAMPLE 1

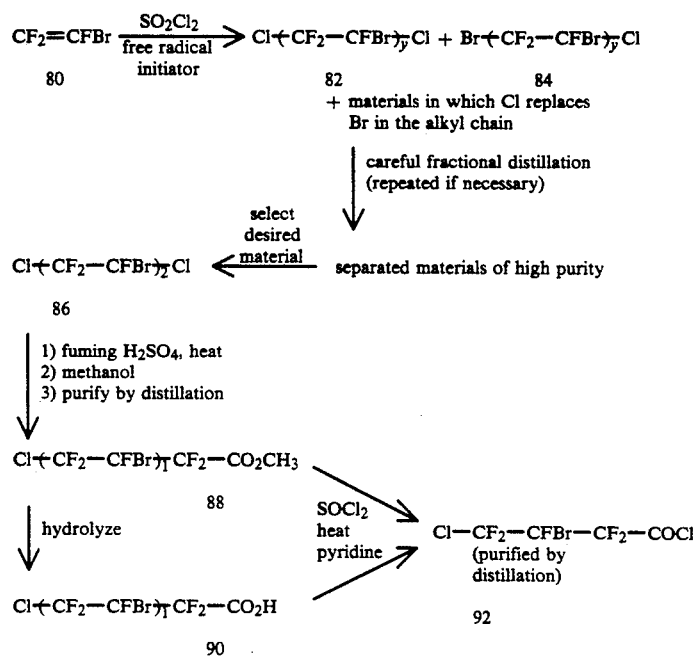

In an alternative procedure, shown in example 2, the same starting materials yield the same initial mixture of adducts and telomers as in example 1, but now the subsequent fractional distillation provides product fractions each having the same carbon number but containing several different materials. In the example these are shown as 94 and 96. The selected product mixture is subjected to sulfuric acid hydrolysis followed by esterification with methanol to yield a mixture of the corresponding methyl esters 98 and 100. This mixture of esters is dehalogenated with zinc and methanol to yield the olefinic ester 102, which is in turn brominated to yield ester 104. Compound 104 can be hydrolyzed to the corresponding carboxylic acid and then converted to the acid chloride 106, or may be converted directly to the acid chloride as shown in the example.

EXAMPLE 2

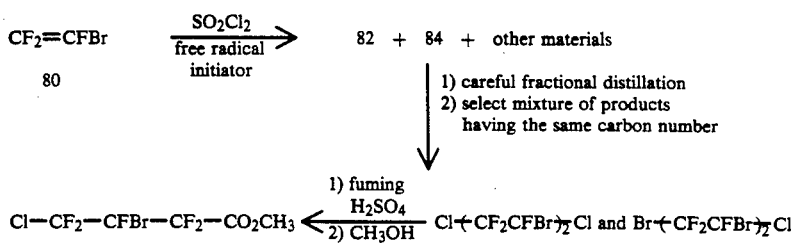

and

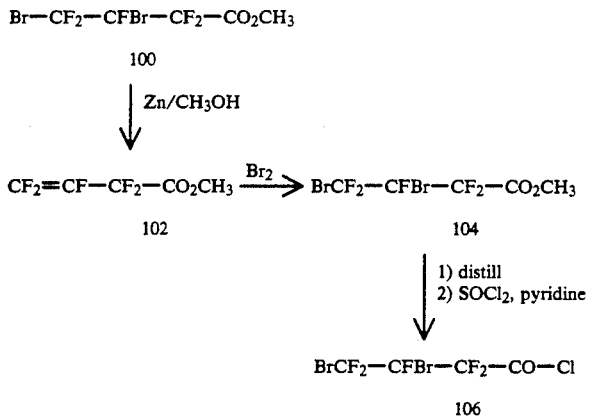

In example 3 trifluorochloroethylene 108 is shown reacting with sulfuryl chloride and a free radical initiator such as azobisisobutyrlnitrile to yield a mixture 110 of adducts and telomers, which is then fractionally distilled to yield a selected telomer 112 which contains 4 monomer units. This is subjected to hydrolysis by fuming sulfuric acid and the resulting acid mixture is esterified to yield a mixture of esters 114 and 116. These materials are separated by distillation, yielding pure ester 116. This material may be hydrolyzed to the corresponding carboxylic acid which can then be converted to the acid chloride 118, or ester 116 can be directly converted to the acid chloride by treatment with thionyl chloride and pyridine, as shown in the example.

EXAMPLE 3 of a free radical initiator to yield a mixture 120 of adducts and telomers. This product mixture is carefully fractionally distilled and a desired telomer is selected, this selected telomer being shown as compound 122 in the example. Upon treatment of compound 122 with fuming sulfuric acid, followed by esterification with methanol, a mixture of esters 124 and 126 is produced. These materials are separated by distillation, yielding pure ester 124. Compound 124 may be hydrolyzed to the corresponding carboxylic acid, which can then be converted to acid chloride 126, or compound 124 can be converted directly to acid chloride 126 by treatment with thionyl chloride and pyridine as shown in the example. Starting with trifluorochlorethylene instead of trifluorobromoethylene would produce similar products, but with chlorine in the chain instead of bromine.

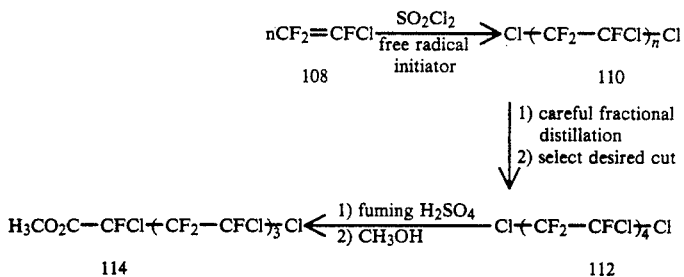

and

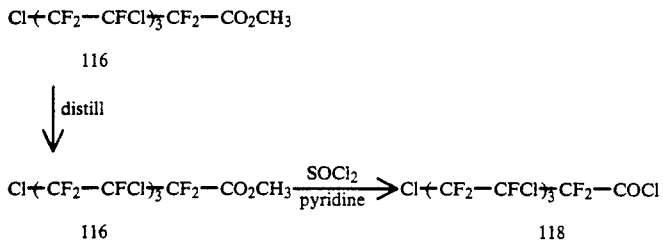

In example 4, trifluorobromoethylene 80 is shown reacting with bromotrichloromethane in the presence

EXAMPLE 4

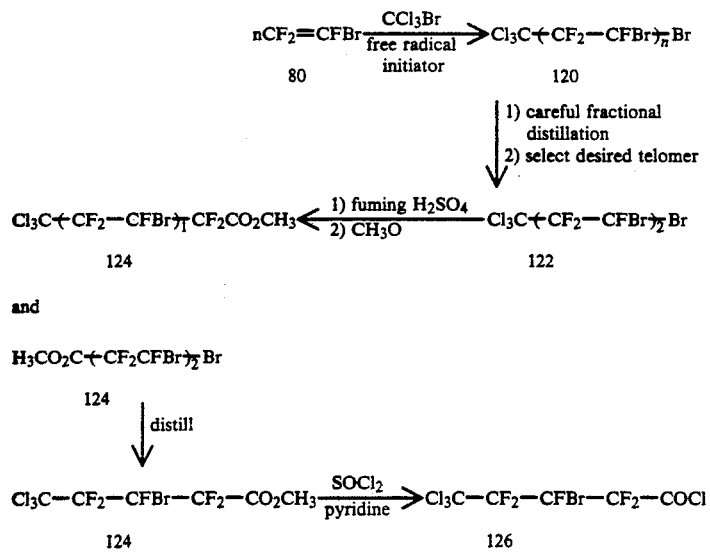

Example 5 shows the reaction of trifluorobromoethylene 80 with trifluoroiodomethane in the presence of a free radical initiator to yield a mixture 128 of adducts and telomers, which is in turn carefully distilled to yield the desired adduct 130. Compound 130 adds across the double bond of tetrachloroethylene 132 to yield adduct 134, which is hydrolyzed and then esterified to yield the ester 136. Ester 136 can be hydrolyzed to the corresponding carboxylic acid, which can in turn be converted to acid chloride 138, or it may be converted directly into acid chloride 138 by treatment with thionyl chloride and pyridine.

adducts and telomers. This is distilled and the desired adduct 146 is selected and then reacted further with halogenated olefin 148 to yield compound 150. Upon mild oxidation compound 150 is converted to halogenated ketone 152, which upon reaction with sulfur tetrafluoride yields the halogenated alkane 154. This is hydrolyzed with fuming sulfuric acid and the resulting mixture is esterified with methanol to produce ester 156. Compound 156 may be hydrolyzed to the corresponding carboxylic acid which then can be converted to the acid chloride 158 by treatment with thionyl chloride, or compound 156 may be converted directly to the acid chloride 158 by treatment with thionyl chloride and pyridine.

EXAMPLE 5

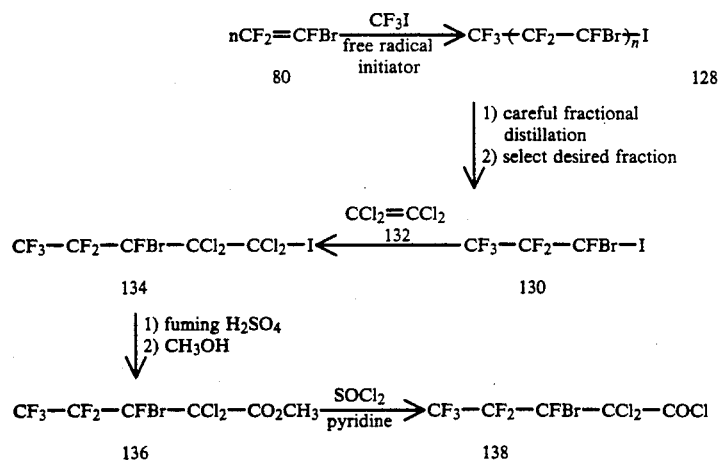

In example 6 dichlorodifluoroethylene 140 is shown reacting in the presence of a free radical initiator with the halogenated alkane 142 to yield a mixture 144 of

EXAMPLE 6

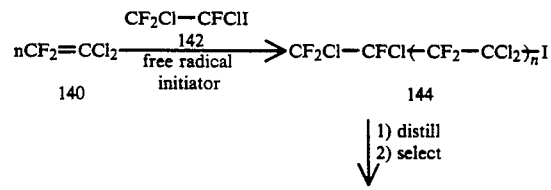

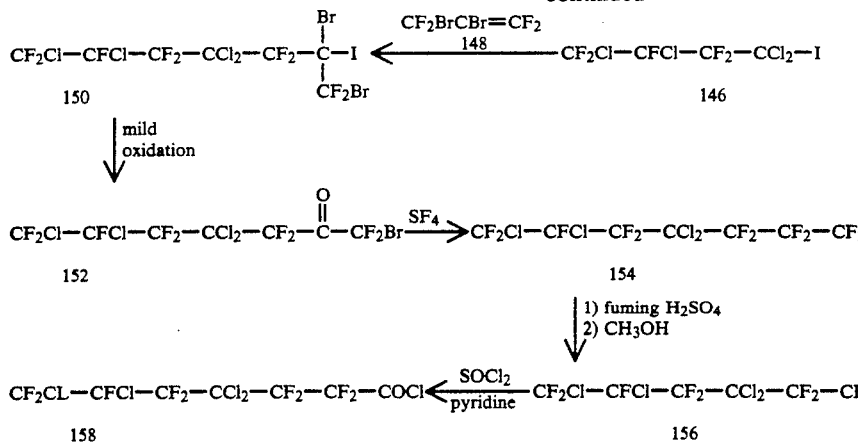

In example 7 halogenated olefin 148 is shown reacting with alkyl halide 142 to yield, after suitable workup, the compound 158. This is then added across the double bond of dichlorodifluoroethylene 140 to yield compound 160 after workup. This is hydrolyzed with sulfuric acid and esterified to yield a mixture of esters from which compound 162 is isolated by appropriate purification procedures. As before, the ester can be hydrolyzed to the corresponding carboxylic acid, which then can be converted to the acid chloride, or compound 162 can be converted directly to the acid chloride by reaction with thionyl chloride and pyridine.

verted to the acid chloride directly by treatment with thionyl chloride and pyridine.

EXAMPLE 8

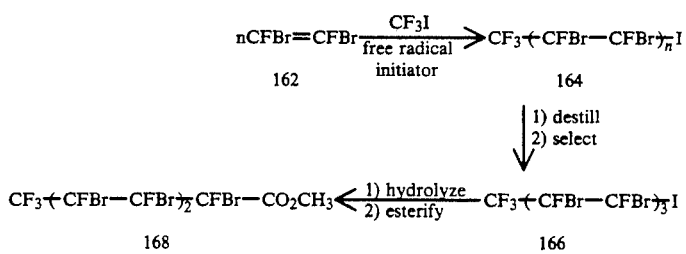

In example 8 the dibromodifluoroethylene 162 is shown reacting with trifluoroiodomethane in the presence of a free radical initiator to yield a mixture 164 of adducts and telomers, from which a particular telomer 166 is obtained by distillation and selection of the appropriate fraction. Compound 166 is hydrolyzed with sulfuric acid and subsequently esterified with methanol to yield ester 168, which can be hydrolyzed to the corresponding carboxylic acid, and this in turn can be readily converted to the acid chloride by treatment with thionyl chloride. Alternatively, compound 168 can be con- In example 9 the known dibromohydroxybenzoic acid 170 is shown reacting with an alcohol to yield ester 172, which upon treatment with a weak base such as potassium carbonate and then an acid chloride yields diester 174. It will be appreciated that R in the alcohol and R' in the acid chloride need not be the same. Preparation of halogenated alcohols and acid chlorides has been discussed above.

EXAMPLE 7

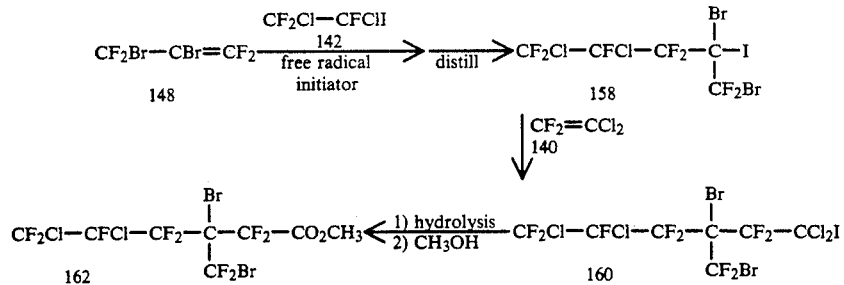

EXAMPLE 9

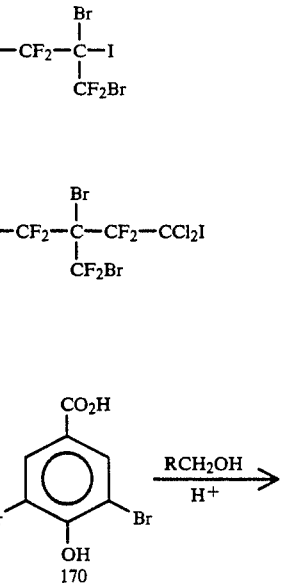

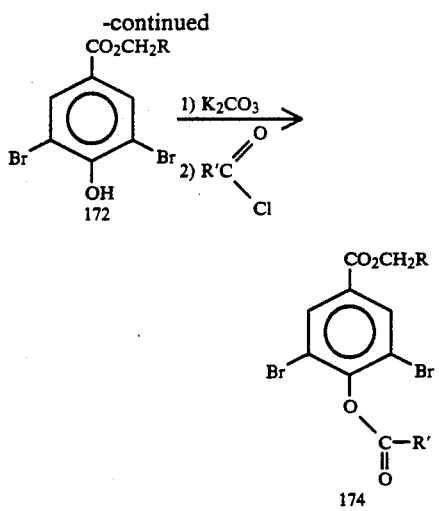

As indicated above, the fluids of the invention find their primary utility as flotation and damping fluids in floated inertial instruments such as certain gyroscopes and accelerometers. Such instruments are illustrated in the figures and discussed below. The fluids referred to are preferably the compounds of the present invention.

Both a gyroscope (gyro) and an integrating pendulous accelerometer are illustrated generically in FIG. 1, which shows a float 10 which is buoyantly supported by a viscous damping fluid 12 within an outer housing 14. Within float 10 is an inertial sensing element 16, which in the case of a gyro is a spinning wheel and in the case of an integrating pendulous accelerometer is a pendulum. At one end of float 10 and outer housing 14 respectively are electromagnetic sensing elements 18 and 18′. At the other end of float 10 and outer housing 14 respectively are electromagnetic torquing elements 20 and 20′. Orthogonal axes 22, 24, and 26 are the input axis, output axis, and spin or pendulous axis, respectively. Forces acting on the devices at input axis 22, i.e., rotation about axis 22 in the case of a gyro and acceleration along axis 22 in the case of an integrating pendulous accelerometer, tend to move float 10 relative to output axis 24, and produce a signal at the sensing elements 18 and 18′. Float motion is offset by a corresponding torque rebalance signal applied to the torquing elements 20 and 20′.

A related instrument is a pendulous integrating gyroscopic accelerometer (PIGA), shown generically in FIG. 1A. In this instrument a pendulous integrating gyroscope (PIG) of FIG. 1 wherein inertial sensing element 16 includes both a spinning wheel and a pendulum is supported on a bearing 28 and spindle 30, which assembly provides 360 degrees of rotational freedom about the input axis 22. The support bearing 28 is mounted on a stationary housing 32. The angular rate of the PIG about axis 22 is applied by a torque motor 34 which is controlled through the signal produced by the sensing elements 18 and 18′. Power from the stationary housing 32 to the rotating PIG is supplied through a slip ring 35. The PIG is shielded from the external environment by an outer housing 36, and is buoyantly supported by a fluid inside housing 36. This reduces accelerator input axis position sensitivity to cross-axis accelerations. This fluid also lubricates slip ring 35 and input axis bearing 28.

EXPERIMENTAL

2,2,3,4,4-pentafluoro-3,4-dibromo-butyryl chloride

To an evacuated 3 liter high pressure reactor containing 10.6 g of azobisisobutyronitrile was added 540 g (4 moles) of $SO_2Cl_2$ and 1,288 g (8 moles) of bromotrifluoroethylene. The reactor was heated, with rocking, to 90° C. and maintained at this temperature for 4 hours. The maximum pressure noted was 400 psig. The volatiles were vented, leaving a mixture of higher boiling telomers. Several similar preparations were conducted to yield a large volume of crude telomer for further purification and conversion to final products. The crude telomer was distilled several times to a final purity of greater than 90% by the procedure described below.

8 liters of crude telomer was placed in a 12 liter round bottom flask attached to a distillation still, the pressure was reduced to about 15 mm of Hg, and the material was distilled quickly to remove low and high boilers. Fractions boiling between 142° C. and 146° C. were collected. These amounted to 5 liters and constituted a mixture containing about 75% of $Cl-(CF_2-CFBr)_2-Cl$ plus some $Br-(CF_2-CFBr)_2-Cl$ and small amounts of other materials.

The collected fractions were distilled using a spinning band still with a reflux ratio of 15:1 and a band spinning rate of 2,500 rpm. Fractions boiling between 145° C. and 176° C. were collected and pooled, yielding 3 liters of the telomer mixture, containing about 88% $Cl(CF_2-CFBr)_2-Cl$. Redistillation under the same conditions yielded 2.5 liters of material having a purity shown to be about 92% by gc and lc.

The purified telomer mixture (500 g) wa refluxed with 500 ml of 33% oleum (fuming sulfuric acid) with constant stirring for 24-26 hrs, then allowed to cool. When the mixture had cooled, 1,000 ml of methanol was added dropwise at a rate sufficient to maintain a gentle reflux. After the methanol addition, the mixture was stirred until cool then allowed to separate, and the lower (organic) layer was withdrawn. The upper layer was shaken with water, allowed to separate, and again the lower organic layer was withdrawn. The two fractions of methyl ester were combined, yielding approximately 500 g of a mixture of methyl esters. This mixture was distilled in a spinning band distillation apparatus using a reflux ratio of 30:1 and a spin rate of 2,500 rpm. Fractions boiling between 157° C. and 162° C. were collected, yielding 420 g of distilled material. The product was redistilled under the same conditions, yielding 375 g of the methyl esters $Cl-CF_2-CFBr-CF_2-CO_2CH_3$ and $Br-CF_2-CFBr-CF_2-CO_2CH_3$. This material was analyzed by gc and shown to be greater than 95% pure chlorine initiated material.

The mixture of purified methyl esters was dissolved in 300 ml of methanol and added dropwise with stirring to a mixture of 159 g of zinc dust and 500 ml of methanol over a period of 4 hrs, maintaining a gentle reflux without supplemental application of heat. After the addition was complete, heat was applied and the mixture was refluxed a further 1.5-2 hrs. The reaction was not allowed to proceed longer than this because prolonged reflux causes the generation of objectionable byproducts in the reaction. The reaction mixture was cooled to room temperature, unreacted zinc was removed by filtration through celite, and the resulting unsaturated product, $CF_2=CF-CF_2-CO_2CH_3$, was washed several times with water, finally yielding 180 g of material. This product was distilled on the spinning band distillation apparatus at a reflux ratio of 30:1 and a spin rate of 2,500 rpm, fractions boiling between 95° C. and 96° C. being collected. The yield after distillation was 117 g. This was redistilled three times under the same conditions until gc/ms analysis showed product of approximately 98% purity. The yield in this step was 100 g of unsaturated ester.

Bromine liquid (89 g) was added dropwise and with stirring to 100 g of the unsaturated ester over a period of 3-4 hrs. After an induction period during which about 10% of the bromine was added, the solution became decolorized and began to boil. Bromine addition was continued at a rate sufficient to maintain gentle refluxing. After about 70% of the bromine had been added the mixture darkened and began to cool. After the bromine addition was complete, the solution was allowed to cool, the product mixture (about 200 ml) was washed with aqueous sodium bisulfite solution, and the organic layer was separated. The yield was 155 g of crude $BrCF_2-CFBr-CF_2-CO_2CH_3$. This product was distilled on the spinning band distillation apparatus at a reflux ratio of 30:1 and a spin rate of 2,500 rpm. Fractions boiling between 171° C. and 175° C. were collected. The product was redistilled under the same conditions to yield 110 g of purified material, shown by gc/ms to be greater than 95% pure. This was stored in a sealed container wrapped in foil.

To 160 g of stirred $BrCF_2-CFBr-CF_2-CO_2CH_3$ in a flask was added 20 g of pyridine. Thionyl chloride (85 g, an excess) was added dropwise over 1.5-2 hrs at a rate sufficient to cause and maintain a gentle reflux. After the addition of thionyl chloride was complete, the mixture was refluxed a further 16 hrs, then cooled to room temperature, allowed to separate, and the acid chloride (lower) layer was removed. This was distilled on the spinning band apparatus under the same conditions as previously employed, using a cold trap on the vents of the apparatus to keep the distillation dry and to trap thionyl chloride and acid vapors. Fractions boiling between 135° C. and 136° C. were collected and combined. The product was redistilled several times to ultimately yield 97 g of $BrCF_2-CFBr-CF_2-COCl$ which was shown by gc/ms to be 99% pure.

(2,4,6-tribromophenyl)-2,2,3,4,4-pentafluoro-3,4-dibromo-butyrate 153 grams of tribromophenol and 36.5 grams of pyridine were dissolved in 350 ml of methylene chloride. 164 grams of 2,2,3,4,4-pentafluoro-3,4-dibromo-butyryl chloride were added dropwise through a dropping funnel with stirring 2.2 grams of dimethylaminopyridine were then added and the solution was stirred. After 0.5 hour, an additional 500 ml of methylene chloride were added and the mixture stirred for an additional 3.5 hours. The mixture was washed in a separatory funnel three times with 500 ml of DI water, then filtered through a column of silica and the solvent evaporated. The material was then chromatographed on a column of silica using FREON 113 (trichlorotrifluorethane) as eluent. The sample (220 grams) was shown to be pure ester by gc/ms. m/e 62 (27%, $C_5H_2$); 69 (21%, $CF_3$); 129 (33%, $CF_2Br$); 131 (100%, $CF_2Br$ and $C_3F_5$); 141 (26%, $C_5H_2Br$); 143 (26%, $C_5H_2Br$); 327, 329, 331, 333 (10%, 27%, 24%, 9% all $C_6Br_3H_2O$). I.R.($\nu$, in $cm^{-1}$)=3110, 3070 (Ar—H); 1800 (C=O); 1550, 1430 (Ar C=C).

(2,4,6-tribromoresorcinyl)-bis-2,2,3,4,4-pentafluoro-3,4-dibromobutyrate 27.9 grams of tribromoresorcinol and 12.7 grams of pyridine were dissolved in 200 ml of methylene chloride. 57.1 grams of 2,2,3,4,4-pentafluoro-3,4-dibromobutyryl chloride were added dropwise through a dropping funnel with stirring. 0.38 grams of dimethylaminopyridine were added and the solution stirred. After 1.5 hours, an additional 100 ml of methylene chloride were added and the mixture stirred for an additional 3 hours. The mixture was washed in a separatory funnel twice with 500 ml of DI water, then filtered through a column of silica and the solvent evaporated. The material was then chromatographed on a column of silica using FREON 113 (trichlorotrifluorethane) as eluent. The sample (59 grams) was shown to be pure ester by gc/ms. m/e 69 (19%, $CF_3$); 129 (33%, $CF_2Br$); 131 (100%, $CF_2Br$ and $C_3F_5$); 289, 291, 293 (7%, 12%, 6% all $CF_2BrCFBrCF_2$). I.R. ($\nu$, in $cm^{-1}$)=3120, 3080 (Ar—H); 1805 (C=O); 1560, 1440 (Ar C=C).]

(2,4,6-trichloro-3-ethyl-phenyl)-2,2,3,4,4-pentafluoro-3,4-dibromobutyrate 46.7 grams of trichloroethylphenol and 16.3 grams of pyridine were dissolved in 300 ml of methylene chloride. 73.3 grams of 2,2,3,4,4-pentafluoro-3,4-dibromobutyryl chloride were added dropwise through a dropping funnel with stirring. 1.0 gram of dimethylaminopyridine was added and the solution stirred. After 1 hour, an additional 200 ml of methylene chloride were added and the mixture stirred for an additional 3 hours. The mixture was washed in a separatory funnel twice with 500 ml of DI water, then filtered through a column of silica and the solvent evaporated. The material was then chromatographed on a column of silica using FREON 113 (trichlorotrifluorethane) as eluent. The sample (100.7 grams) was shown to be Pure ester gc/ms. m/e (chemical ionization) 69 (22%, $CF_3$); 109, 111, 113 (9%, 3%, 0.5%, all $C_3H_3CL_2$); 123, 124, 125, 127 (12%, 4%, 18%, 5%, unassigned); 129 (35%, $CF_2Br$); 131 (100%, $CF_2Br$ and $C_3F_5$); 159, 160, 161, 162, 163, 165 (21%, 21%, 13%, 16%, 2%, unassigned); 223, 225, 227, 229 (70%, 65%, 20%, 2% (all $C_8H_6Cl_3O$); 289, 291, 293 (4%, 9%, 4% all $C_3F_5Br_2$); 540, 542, 544, 546, 548, 550 (2%, 5%, 7%, 3%, 0.6%, 0.1%, molecular ion). I.R.($\nu$, in $cm^{-1}$)=3080 (Ar—H); 2970, 2930, 2870 (R—H); 1805 (C=O); 1570, 1450 (Ar C=C).

(2,4,6-triiodophenyl)-2,2,3,4,4-pentafluoro-3,4-dibromo-butyrate 100 grams of triiodophenol were dissolved in 100 ml of pyridine with warming to 50° C. 75 grams of 2,2,3,4,4-pentafluoro-3,4-dibromo-butyryl chloride were added dropwise through a dropping funnel with stirring at such a rate that the temperature did not rise above 65° C. The mixture was stirred at 50° C. for an additional 30 minutes, then overnight at room temperature. The mixture was washed in a separatory funnel three times with 500 ml of DI water, then filtered through a column of silica and the solvent evaporated. The material was then chromatographed on a column of silica using FREON 113 (trichlorotrifluroethane) as eluent. Chromatography on silica gave 75.5 grams of material 99% pure. The material solidified at room temperature and has a melting point of 50° C. I.R.($\nu$, in $cm^{-1}$)=3050, 3090 (Ar—H); 1800 (C=O); 1570, 1415 (Ar C=C). m/e 62 (47%, $C_5H_2$); 69 (18%, $CF_3$); 129

(22%, $CF_2Br$); 131 (70%, $CF_2Br$ and $C_3F_5$); 189 (60%, $C_5H_2I$); 344 (56%, $C_6H_2I_2O$); 471 (100%, $C_6H_2I_3O$).

Synthesis of Meta Substituted Triiodophenols

Though a large number of halogenated phenols have been reported in the literature, one skilled in the art is not limited to such reported halogenated phenolic compounds. For example, a procedure reported for the synthesis of triiodophenol (P. Chabrier, J. Seyden-Penne, and A. M. Fouace, *Compt. Rend.*, 245, 174 (1957)) was used with meta bromophenol, meta ethylphenol and meta methylphenol to form the corresponding meta substituted triiodo compounds, which were then converted to the desired esters. The above paper is hereby incorporated by reference.

(2,4,6-triiodo-3-bromo-phenyl)-2,2,3,4,4-pentafluoro-3,4-dibromobutyrate 20.3 grams of 3-bromo-2,4,6-triiodophenol (m.p 155°–157° C.) were dissolved in 50 ml of pyridine 13.0 grams of 2,2,3,4,4-pentafluoro-3,4-dibromo-butyryl chloride were added dropwise through a dropping funnel with stirring. The mixture was stirred overnight at room temperature. The mixture was washed in a separatory funnel twice with 250 ml of DI water, then filtered through a column of silica and the solvent evaporated. The material was then chromatographed on a column of silica using FREON 113 (trichlorotrifluroethane) as eluent. The sample (25 grams), which slowly crystallized at room temperature, was shown to be pure ester (97%) by gc/ms. It is suitable for use as a fluid above its melting point of 56°–57° C. m/e (chemical ionization) 129 (21%, $CF_2Br$); 131 (100%, $CF_2Br$ and $C_3F_5$); 140 (13%, $C_5HBr$); 142 (13%, $C_5HBr$); 188 (14%, $C_5HI$); 267, 269 (11%, 10% $C_5BrIH$); 315 (4%, $C_5I_2H$); 422, 424 (6%, 7%, $C_6I_2HBrO$); 549, 551 (5%, 4%, $C_6I_3HBrO$); 866, 868, 870, 872 (0.2%, 0.6%, 0.4%, 0.2%, molecular ion). I.R.($\nu$, in cm$^{-1}$) =3080 (Ar—H); 1800 (C=O); 1550, 1520 (Ar C=C).

(3-methyl-2,4,6-triiodophenyl)-2,2,3,4,4-pentafluoro-3,4-dibromobutyrate 10 grams of 3-methyl-2,4,6-triiodophenol and 1.6 grams of pyridine were dissolved in 300 ml of methylene chloride. 7.3 grams of 2,2,3,4,4-pentafluoro-3,4-dibromo-butyryl chloride were added dropwise through a dropping funnel to the stirring phenol/pyridine solution. 0.2 gram of dimethylaminopyridine was added. The mixture was stirred for an additional 4 hours, then was washed twice with 500 ml DI water in a 1,000 ml separatory funnel, filtered through a column of silica, and the solvent evaporated. The material was then chromatographed on a column of basic aluminum oxide using FREON 113 (trichlorotrifluroethane) as eluent. A final yield of 11 grams of ester was obtained. The material was shown by gc/ms to be pure ester I.R ($\nu$, in cm$^{-1}$) =3100, 3070 (Ar—H); 2950, 2920 (Me C-H); 1800 (C=O); 1545, 1520 (Ar C=C). m/e 76 (61%, $C_6H_4$); 129 (40%, $CF_2Br$); 131 (100%, $CF_2Br$ and $C_3F_5$); 203 (61%, $C_5HICH_3$); 231 (28%, $C_6HICH_3O$); 358, (42%, $C_6HI_2CH_3O$); 485, (66%, $C_6I_3HCH_3O$).

(3-ethyl-2,4,6-triiodophenyl)-2,2,3,4,4-pentafluoro-3,4-dibromobutyrate 20 grams of 3-ethyl-2,4,6-triiodophenol and 3.15 grams of pyridine were dissolved in 300 ml of methylene chloride. 14.1 grams of 2,2,3,4,4-pentafluoro-3,4-dibromo-butyryl chloride were added dropwise through a dropping funnel to the stirring phenol/pyridine solution. 0.2 gram of dimethylaminopyridine was added. The mixture was stirred for an additional 4 hours, then was washed three times with 500 ml DI water in a 1,000 ml separatory funnel, filtered through a column of silica, and the solvent evaporated. The material was then twice chromatographed on columns of silica using FREON 113 (trichlorotrifluroethane) as eluent. A final yield of 29 grams of ester was obtained. The material was shown by gc/ms to be pure ester. I.R.($\nu$, in cm$^{-1}$) =3090, 3070 (Ar—H); 2970, 2930, 2870 (Me C—H); 1800 (C=O); 1545, 1530 (Ar C=C). m/e 69 (31%, $CF_3$); 89 (70%, $C_7H_5$); 129 (42%, $CF_2Br$); 131 (100%, $CF_2Br$ and $C_3F_5$); 357 (34%, $C_7H_3I_2O$); 372 (34%, $C_2H_5C_6HI_2O$); 499 (49%, $C_2H_5C_6HI_3O$).

(2,3,4,6-tetrabromophenyl)-2,2,3,4,4-pentafluoro-3,4-dibromobutyrate 150 grams of 2.3.4.6-tetrabromophenol and 3.15 grams of pyridine were dissolved in 500 ml of methylene chloride. 140 grams of 2,2,3,4,4-pentafluoro-3,4-dibromo-butyryl chloride were added dropwise through a dropping funnel to the stirring phenol/pyridine solution. 2.4 grams of dimethylaminopyridine were added. The mixture was stirred overnight (16 hours), then was washed three times with 500 ml DI water in a 1,000 ml separatory funnel, filtered through a column of silica, and the solvent evaporated. The material was then chromatographed three times on columns of basic aluminum oxide using FREON 113 (trichlorotrifluroethane) as eluent. A final yield of 230 grams of ester was obtained. The material was shown by gc/ms to be pure ester ( 99%). I.R.($\nu$, in cm$^{-1}$)=3100, 3060 (Ar—H); 1805 (C=O); 1545, 1535 (Ar C=C). m/e 61 (14%, $C_5H$); 69 (15%, $CF_3$); 129 (26%, $CF_2Br$); 131 (100%, $CF_2Br$ and $C_3F_5$); 140 (13%, $C_5HBr$); 142 (13%, $C_5HBr$); 219, 221, 223 (9%, 17%, 8%, all $C_5Br_2H$); 405, 407, 409, 411, 413 (2%, 11%, 14%, 7%, 2%, all $C_6Br_4HO$).

Methyl-3,5,7,8-tetrachloro-2,2,3,4,4,5,6,6,7,8,8-undecafluoro octanoate

A 5 gal Hastelloy C stirred autoclave fitted with a dip tube and valve, overgas valve, thermowell, 1,000 psig teflon-coated Inconel rupture disc was set up in a safety containment tank having a 200 psi rupture disc. Reagent grade concentrated sulfuric acid (2,800 ml) was measured into a dry flask, and 1,400 ml of fuming sulfuric acid (27–33% $SO_3$) were added carefully with stirring, care being taken to minimize exposure to atmospheric moisture. The autoclave was evacuated to a pressure of approximately 28 inches of mercury by means of an aspirator, then sealed off to maintain the vacuum. 5 kg of 98% pure CTFE tetramer, Cl($CF_2$—$CFCl$)$_4$—Cl, were weighed into a suitable container, connected to the autoclave via tubing, then drawn into the autoclave reactor through the liquid sampling valve and dip tube, by the residual vacuum. The autoclave stirrer was adjusted to 500 rpm. Next, the sulfuric acid solution was similarly drawn into the reactor. Pressure and temperature sensors were set to sound alarms at 500 psig and 240° C. respectively. The temperature of the reaction was raised in 50° C. increments every 0.5 to 0.75 hrs until a temperature of 215° C. was reached. This temperature was then maintained for the remainder of the predetermined 17 hr run time. At the conclusion of the run, the reaction mixture was cooled to 60° C. and sampled to test for completeness of reaction.

A 10 ml representative sample was removed, carefully added to an excess of methanol, and stirred for 10 minutes while being heated. After cooling the mixture, water was added, the mixture was allowed to separate, and the bottom layer was isolated and analyzed by gc. Test criteria were as follows. If the amount of monoester was found to be less than 70% of the mixture, the amount of starting tetramer greater than 10%, and the amount of diester less than 15%, the reaction was continued for an additional 4 hrs. On the other hand, if the monoester constituted at least 70% of the mixture, the starting tetramer constituted less than 10%, and the diester constituted 15% or greater, the reaction was considered complete.

At the completion of the reaction, heating was discontinued and the reaction mixture was cooled to approximately 50° C. The mixture was then slowly discharged into a 22 liter three-neck flask, the transfer being accomplished by providing a suitable connecting tube between the dip tube of the autoclave and a neck of the receiving flask, then evacuating the receiving flask slightly by means of an aspirator. The transferred reaction mixture was allowed to settle overnight, separating into two layers.

The bottom layer of the hydrolyzed mixture was separated and added rapidly to 6 liters of methanol in a 12 liters flask, then refluxed overnight. The resulting mixture was then allowed to separate and the colorless ester bottom layer was drawn off. The top layer was extracted twice with FREON 113 and added to the ester lower layer. The resulting mixture of ester and FREON 113 was neutralized with sodium bicarbonate, washed with D.I. water, and distilled. Distillation at a head temperature of 72° C. and 0.16 ml of mercury produced the desired methyl ester in 99+% purity.

(2,4,6-tribromophenyl)-2,2,3,4,4-pentafluoro-3-bromo-4-chlorobutyrate

This was prepared like the corresponding dibromo material, but using 2,2,3,4,4-pentafluoro-3-bromo-4-chlorobutyryl chloride purchased from PCR. I.R.=1,800 cm$^{-1}$. m/e 69(49%,CF$_3$); 85, 87 (45%, 17%, CF$_2$Cl); 129 (31%, CF$_2$Br); 131 (99%, CF$_2$Br, C$_3$F$_5$); 141,143 (48%, 47%, C$_5$H$_2$Br); 299, 301, 303, 305 (18%, 44%, 42%, 14%, C$_5$Br$_3$H$_2$); 327, 329, 331, 333 (39%, 100%, 96%, 34%, C$_6$Br$_3$H$_2$O); 602,604,605,606,608,610 (17%, 28%, 24%, 9%, 1%, C$_{10}$H$_2$Br$_4$ClF$_5$O$_2$).

Pin-on-Disc Wear Test for Measurement of Qualitative Wear Associated With Use of the Compounds of the Invention as Lubricants In pin-on-disc testing a weighted pin (preferably having a radius at the tip) was placed in contact with a rotating metallic disc, and the wear track on the disc as well as the torque required to restrain the pin were measured. The equation relating the torque to the friction coefficient is $$T = \mu PR$$

where $\mu$ is the friction coefficient, P is the load on the pin, and R is the wear track radius. The disc was typically of brass, the surface of which was plated successively with nickel and with about 10 microns of gold. The weight on the pin was typically 250 g. The pin itself was typically an alloy of gold, specifically, Neyoro G.

Tests of several experimental fluids and appropriate controls were run on each test disc, krytox being used as the standard.

The wear tester is an apparatus for keeping two contacting specimens in relative motion under a known load. It has a means for measuring the restraining force or the torque developed, thus permitting the coefficient of friction to be determined, as indicated above.

Measurement of the frictional torque (and hence the coefficient of friction) developed between the two specimens was accomplished with a Bendix double reed flex-pivot coupled to a microsyn signal generator rotor and provided with variable damping. The flex-pivot is basically a linearly elastic torsional spring, the angular deflection of which is proportional to an applied torque. In the test procedure, the stationary specimen is mounted on the flex-pivot. When the disc upon which the pin is riding rotates, a torque is applied to the pin and hence to the arm of the flex-pivot. Since the signal generator rotor moves from the null position when torque is applied, a voltage signal is generated the amplitude of which is proportional to the magnitude of the applied torque.

The width and depth of the wear track in the disc were measured by a Sloan Dektak II Profilometer at several points along the wear track, and averaged.

Test results on a given plate can be compared, but it is more difficult to compare tests run on different plates, since no two plates are exactly identical.

The above-described wear tester and its method of use are more fully described in Report No. C-5413 by K. E. Koehler of The Charles Stark Draper Laboratory, Inc., 1981, which report is hereby incorporated by reference.

In Table VII below are shown the results of qualitative pin-on-disc wear tests of several of the exemplary compounds of the invention, relative to Krytox. It will be noted that the compounds of the invention performed better than Krytox in reducing wear.

TABLE VII

| Material Tested[a] | Wear Data (Pin-on-Disc)* | | |
|---|---|---|---|
| | Wear Track Width[b] | Wear Track Depth[b] | Wear Area[b] |
| Krytox | 1.00 | 1.00 | 1.00 |
| 1 | 1.00 | 0.50 | 0.50 |
| 2 | 1.00 | 0.50 | 0.50 |
| 7 | 1.00 | 0.50 | 0.50 |

*Tests were run at 1 rpm under a 250 g load for 24 hours at 1 RPM.
[a]numbers shown in the first column refer to synthesized exemplary compounds of TABLE I
[b]relative to Krytox Although the fluids of the invention and their methods of preparation have been exemplified by specific compounds and reactions, those skilled in the art will recognize that certain other compounds and reaction conditions are within the intended scope of the invention. Accordingly, the invention is to be limited only by the scope of the appended claims.

What is claimed is:

1. A method for lubricating a floated inertial instrument, comprising the steps of:
   providing an inertial instrument having a housing for containing an inertial sensing element and at least one axis bearing; and
   introducing into said housing, said sensing element, and said bearing, a lubricating compound having the general formula

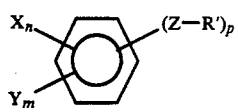

wherein:

X is a halogen selected from the group consisting of F, Cl, Br, and I, and n=1-5, the sum of the masses of said halogens being at least 90;

Y is a substituent selected from the group consisting of —R, —OR, —CO₂R, and —NO₂, wherein R is a straight, branched, or cyclic alkyl or haloalkyl group containing 1-4 carbon atoms, and m=0-2;

Z is

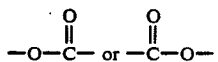

R' is a straight, branched, or cyclic haloalkyl group containing 2-8 carbon atoms and at least one F atom, the remaining halogen atoms of said R' group being selected from the group consisting of F, Cl, and Br, the halogens of said R' group replacing more than 60% of the hydrogen atoms in a corresponding unhalogenated R' group, and wherein P=1-3.

2. The method of claim 1 further comprising the step of providing an inertial instrument which further contains a slip ring, said slip ring being in electrical contact with said inertial sensing element.

3. The method of claim 1 further comprising introducing a perfluoropolyether into said housing.

4. The method of claim 1 wherein at least one substituent X is selected from the group consisting of bromine and iodine.

5. The method of claim 1 wherein at least one substituent Y is methyl or ethyl.

6. The method of claim 1 wherein said floated inertial instrument is a gyroscope.

7. The method of claim 1 wherein said floated inertial instrument is an integrating gyroscopic accelerometer.

8. A method for lubricating a bearing supporting a floatable component, said method comprising the steps of:

providing a housing containing said bearing supporting said floatable component; and introducing into said housing and said bearing, a lubricating compound having the general formula

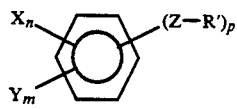

wherein:

X is a halogen selected from the group consisting of F, Cl, Br, and I, and n=1-5, the sum of the masses of said halogens being at least 90;

Y is a substituent selected from the group consisting of —R, —OR, —CO₂R, and —NO₂, wherein R is a straight, branched, or cyclic alkyl or haloalkyl group containing 1-4 carbon atoms, and m=0-2;

Z is

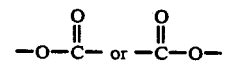

R' is a straight, branched, or cyclic haloalkyl group containing 2-8 carbon atoms and at least one F atom, the remaining halogen atoms of said R' group being selected from the group consisting of F, Cl, and Br, the halogens of said R' group replacing more than 60% of the hydrogen atoms in a corresponding unhalogenated R' group, and wherein p=1-3.

9. A method for lubricating a floated inertial instrument, comprising the steps of:

providing an inertial instrument having a housing for containing an inertial sensing element and at least one axis bearing; and introducing into said housing, said sensing element, and said bearing, a lubricating compound, said compound consisting of a substituted or unsubstituted halogenated aryl group linked by an ester to from one to three halogenated alkyl groups, said halogenated aryl group containing from 1-5 halogen atoms selected from the group consisting of F, Cl, Br, and I, the sum of the masses of said halogens being at least 90;

said substituted halogenated aryl group having, zero, one or two substituents selected from the group consisting of —R, —OR, —CO₂R, and —NO₂, wherein R is a straight, branched, or cyclic alkyl or haloalkyl group containing 1-4 carbon atoms;

said ester linkage being of the form

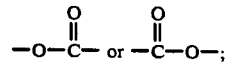

and said halogenated alkyl group being a straight, branched, or cyclic haloalkyl group containing 2-8 carbon atoms and at least one F atom, the remaining halogen atoms of said halogenated alkyl group selected from the group consisting of F, Cl, and Br, the halogens of said haloalkyl group replacing more than 60% of the hydrogen atoms in a corresponding unhalogenated alkyl group.

* * * * *

UNITED STATES PATENT AND TRADEMARK OFFICE
CERTIFICATE OF CORRECTION

PATENT NO. : 5,248,432
DATED : September 28, 1993
INVENTOR(S) : John R. Williams It is certified that error appears in the above-identified patent and that said Letters Patent is hereby corrected as shown below:

In the Title "HALOGENATED ARYL ESTER DAMPING FLUID AND LUBRICANTS" should read -- METHOD FOR LUBRICATING A FLOATED INERTIAL INSTRUMENT--.

Column 2, line 51, "o(" should read --of--.

Column 4, line 29, "located 8" should read --located ß--.

Column 12, Table III, line 46, "1562" should read --1462--.

Column 14, Table III, line 8, "-2-4,6-triiodo" should be deleted where "IV 1045" appears in the other columns on the same line thereof.

Column 16, line 12, "Table v" should read --Table V--.

Column 21, in Example 4, the section which reads "2) $CH_3O$" should read --2) $CH_3OH$--.

Column 26, line 34, "wa" should read --was--.

Column 27, line 53, "stirring" should read --stirring.--.

Column 28, line 38, "Pure" should read --pure--.

UNITED STATES PATENT AND TRADEMARK OFFICE
CERTIFICATE OF CORRECTION

PATENT NO. : 5,248,432
DATED : September 28, 1993
INVENTOR(S) : John R. Williams It is certified that error appears in the above-indentified patent and that said Letters Patent is hereby corrected as shown below:

Column 30, line 21, "2.3.4.6-tetrabromophenol" should read --2, 3, 4, 6-tetrabromophenol--.

Signed and Sealed this

Twentieth Day of September, 1994

Attest:

BRUCE LEHMAN

Attesting Officer

Commissioner of Patents and Trademarks